(12) United States Patent
Erickson et al.

(10) Patent No.: US 8,944,245 B2
(45) Date of Patent: *Feb. 3, 2015

(54) DISPENSING STRIP FOR NEEDLE ASSEMBLIES

(75) Inventors: Thomas E. Erickson, Crosslake, MN (US); James J. Erickson, Mound, MN (US); Timothy A. Bachman, St. Paul, MN (US)

(73) Assignee: UltiMed, Inc., Excelsior, MN (US)

( * ) Notice: Subject to any disclaimer, the term of this patent is extended or adjusted under 35 U.S.C. 154(b) by 984 days.

This patent is subject to a terminal disclaimer.

(21) Appl. No.: 12/492,688

(22) Filed: Jun. 26, 2009

(65) Prior Publication Data

US 2009/0255839 A1 Oct. 15, 2009

Related U.S. Application Data

(63) Continuation of application No. 10/862,838, filed on Jun. 7, 2004, now Pat. No. 7,556,149.

(51) Int. Cl.
*B65D 83/00* (2006.01)
*A61M 5/32* (2006.01)
*A61M 5/00* (2006.01)

(52) U.S. Cl.
CPC ............. *A61M 5/3205* (2013.01); *A61M 5/002* (2013.01)
USPC ............................ 206/366; 206/438; 206/345

(58) Field of Classification Search
USPC ................. 206/338, 346, 347, 343, 345, 339, 206/363–367, 438, 571, 820; 221/70, 69, 221/103–105
See application file for complete search history.

(56) References Cited

U.S. PATENT DOCUMENTS

| | | | |
|---|---|---|---|
| 3,858,722 A | | 1/1975 | Haas |
| 3,861,560 A | * | 1/1975 | Entwistle et al. ............... 221/70 |
| 4,004,683 A | | 1/1977 | Pomeroy et al. |
| 4,209,091 A | * | 6/1980 | Lieberman .................... 206/704 |
| 4,436,205 A | * | 3/1984 | Horii ............................. 206/530 |
| 4,807,753 A | | 2/1989 | Goldstein |
| 5,152,394 A | | 10/1992 | Hughes |
| 5,181,619 A | | 1/1993 | Noble |
| 5,240,108 A | | 8/1993 | Tonna |
| 5,245,117 A | * | 9/1993 | Withers et al. ................ 588/249 |
| 5,409,113 A | | 4/1995 | Richardson et al. |
| 5,494,158 A | | 2/1996 | Erickson |
| 5,545,145 A | | 8/1996 | Clinton et al. |
| 5,944,700 A | * | 8/1999 | Nguyen et al. ................ 604/263 |
| 5,971,966 A | | 10/1999 | Lav |

(Continued)

FOREIGN PATENT DOCUMENTS

| | | |
|---|---|---|
| EP | 0497890 B1 | 5/1990 |
| WO | 9526993 | 10/1995 |
| WO | 02098477 A2 | 12/2002 |

OTHER PUBLICATIONS

Ward, "New Frontiers in Polymer Surface Modification", Medical Device Link, Nov. 2007, pp. 1-3.

*Primary Examiner* — Steven A. Reynolds
(74) *Attorney, Agent, or Firm* — Seager, Tufte & Wickhem LLC

(57) ABSTRACT

A sharps container for (i) safe transportation and dispensing of a large number of unused pen needle assemblies, and (ii) safe storage of used pen needle assemblies. The unused pen needle assemblies may be connected to a flexible tape and are removed from a storage receptacle via an exit opening in the receptacle.

11 Claims, 5 Drawing Sheets

(56) References Cited

U.S. PATENT DOCUMENTS

| | | |
|---|---|---|
| 6,685,017 B2 | 2/2004 | Erickson |
| 6,715,608 B1 * | 4/2004 | Moore .......................... 206/397 |
| 7,163,549 B2 | 1/2007 | Crank et al. |
| 7,556,149 B2 * | 7/2009 | Erickson et al. .............. 206/366 |
| 2003/0132129 A1 | 7/2003 | Erickson |
| 2004/0097882 A1 | 5/2004 | DiBiasi et al. |
| 2006/0095067 A1 | 5/2006 | Lin et al. |
| 2007/0265655 A1 | 11/2007 | Renati et al. |
| 2008/0034972 A1 | 2/2008 | Gough et al. |

* cited by examiner

DISPENSING STRIP FOR NEEDLE ASSEMBLIES

RELATED APPLICATIONS

This application is a continuation application of U.S. application Ser. No. 10/862,838 filed Jun. 7, 2004.

BACKGROUND AND FIELD OF THE INVENTION

This invention relates specifically to multi-functional "sharps" containers which provide (i) safe transportation of the container and a large number, i.e., a "bulk" quantity of unused pen needle assemblies (sometimes hereafter referred to as "PNAs") therein, (ii) the safe sequential dispensing of the aforesaid unused PNAs from the container and (iii) the safe sequential feeding or insertion of used PNAs into the container for safe storage therein.

Because of well known health issues, the safe disposal of medical and other syringes has long been a high priority for the related professions and industries. The prior art containers for such syringes are commonly termed "sharps" containers and many configurations of these are found in public venues such as hospitals, medical clinics, and retail establishments. These containers are usually securely attached to some base means and have a lock means to permit controlled and safe disposal of used "sharps."

There are also prior art "portable" sharps containers for syringes. Examples of prior art portable "sharps" containers for syringes are U.S. Pat. No. 5,494,158 and U.S. Pat. No. 6,685,017; these sharps containers necessarily are large because of the elongated length of the syringes.

Medical delivery pens have, more recently, become widely used instead of or in addition to syringes, e.g., by diabetics, who frequently inject themselves several times a day with accurately measured, adjustable amounts of insulin or other medication. Medical delivery pens include a reservoir of medication and a distal end adapted to be attached (usually by thread means) to a pen needle assembly. As is well known (see, for example FIG. 1 of U.S. Pat. No. 5,545,145), the pen needle assembly has (within an outer, generally cylindrical shield 28) a generally cylindrical housing 26 within which is mounted an axially extending hollow needle 21, (i) the proximal end 24 of which punctures a seal in the distal end 16 of the medical delivery pen 10 (to allow the flow there-through of medication) when the delivery pen is screwed into the proximal end of the pen needle cylindrical housing 26, and (ii) the distal end 22 of which is for insertion into tissue of the person requiring the medication. The pen needle assemblies typically include a removable thin sterile seal covering the proximal (large diameter) end of the said outer shield and a removable tube-like shield covering the distal portion of the hollow needle. The assembled pen needle assembly is then factory sterilized. The user of a pen needle assembly removes the seal from the outer shield, screws the pen into the proximal end of the pen needle housing, removes the outer and tube-like shields, sets the medical delivery pen for the desired dose of medication, and then inserts the distal end of the pen needle into the target tissue following which the medical delivery pen is actuated to deliver the desired dose of medication through the hollow needle into said tissue.

Many diabetics routinely administer medication to themselves several times a day by injection of a pre-selected quantity of insulin (or medical substitute medication) in liquid form; the correct amount of medication can be determined from prior professional medical instruction or by use of convenient blood analysis kits which are small, compact and provide rapid indicators of the user's blood sugar level. The several daily injections are, at least in part, done away from the diabetic's home or residence which has made the use of medical delivery pens widespread. The aforesaid testing kits and the medical delivery pens are relatively small in size and can easily fit within a woman's purse or equivalent. A typical scenario for a diabetic at a restaurant is, before a meal, to use the blood sugar testing kit to obtain an indicator of his or her blood sugar level. This information then facilitates programming or adjusting the medical delivery pen to deliver the desired quantity of medication. Then the pen with an attached PNA (sans the outer protective shield) is used to inject the medication. These steps require a relatively short length of time and can be done with minimum loss of privacy.

In a perfect world, the user of a pen needle assembly would, after the first use of a pen needle assembly, carefully detach the used pen needle assembly from the medical delivery pen and safely dispose said assembly. The approved procedure is (i) insertion of the distal end of the needle into the tube-like shield, NS (sometimes omitted) and thence the shielded needle and cylindrical housing into the outer shield, (ii) unscrewing of the medical delivery pen from the proximal end of the pen needle cylindrical housing, and (iii) careful placement of the used pen needle assembly into a safe sharps container. Alas, the recommended procedure is not always followed. Used (and potentially dangerous) pen needles, with or without outer shields, are routinely left in unsafe places where third parties may unwittingly be "stuck." Examples of such unsafe places are purses, the seat pockets on the back of aircraft seats, private and public wastebaskets, garbage cans, dumpsters and empty milk or other unsafe containers.

One prior art example of a container for unused and used pen needle assemblies is U.S. Pat. No. 5,545,145 which shows a tube containing a small number of unused pen needle assemblies arranged in axial alignment. This patent also teaches that, as unused assemblies are removed from one end of the tube, then a used assembly may be inserted into the tube from the other end. The tube is adapted to be attached to the side of a medical delivery pen. This arrangement has significant shortcomings. The capacity is quite limited and, potentially dangerous "sticks" could occur when a user tries to insert a used assembly (with or without the protective outer shield) into the used end of the tube.

SUMMARY OF THE INVENTION

This invention covers multi-functional "sharps" containers which provide (i) safe transportation of the container and a large number (bulk quantity) of unused PNAs therein, (ii) the safe sequential dispensing of the unused PNAs from the container and (iii) the safe sequential feeding or insertion of used PNAs into the container for safe storage therein; the invention facilitating the ultimate safe disposal of the used PNAs.

The present invention provides a safe, space efficient sharps container for providing the aforesaid functions. The invention provides a container which is especially useful for an individual such as a diabetic who may require several daily doses of medication, which doses are required throughout the day (frequently at meal time) and thus may occur at the users residence as well as at other locations such as the user's place of work, at a restaurant, in an automobile or aircraft, etc. The container which on the one hand can contain "bulk" quantities of unused PNAs and provide safe storage for similar quantities of used PNAs, on the other hand, can be relatively compact and sized to fit within a woman's purse or equivalent.

In broad terms the present invention provides a container comprising an open-topped receptacle, a cover member, and a manually movable means which may be rotated from a "closed" position to an "open" position. In the open position the manually movable means may receive a used pen needle assembly. Then manual rotation of the movable means to the closed position facilitates the discharge of the used pen needle assembly into the receptacle. The receptacle is sized to hold a plurality of used pen needle assemblies (with or without the outer shields). The receptacle is a cup-like vessel which, although of a size to hold a large number of used pen needle assemblies, may at the same time be "small" and/or "thin" enough to be conveniently portable for travel with the user. The receptacle includes internal means for segregating unused PNAs from used PNAs; such internal means may be a fixed partition or may be a movable dividing tray means.

The cover member is sized to fully cover the open-topped receptacle and has a top surface.

The manually movable means, in one embodiment, is a rotatable hatch means. The rotatable hatch means is adapted to be mounted in an opening in the top of the cover for rotation between a closed position and an open position. The hatch means includes a top portion, a bottom portion, and a pair of axially spaced-apart side portions which collectively define a cup-like receiving means for only a single PNA when the hatch means is in the open position. Other means for disposing of or discharging used PNAs into the receptacle are also shown.

The receptacle also includes an exit opening sized to facilitate sequential withdrawal therethrough of unused PNAs. Several alternatives are shown for storing the PNAs and the sequential dispensing of same through an exit opening in the receptacle.

The use of the container by the user is easy. For example, when using the embodiment comprising the above described hatch means, the hatch means is manually rotated to the open position, the used pen needle assembly is placed or dropped into the hatch means, and then the hatch means is manually rotated to the closed position. When the hatch means is closed, then the used pen needle assembly falls into the receptacle. Again, the used PNAs will be stored (hygienically separated from the unused PNAs) in either a space defined in part by a fixed partition or by a movable dividing tray means.

DETAILED DESCRIPTION OF THE INVENTION

Figure 1:
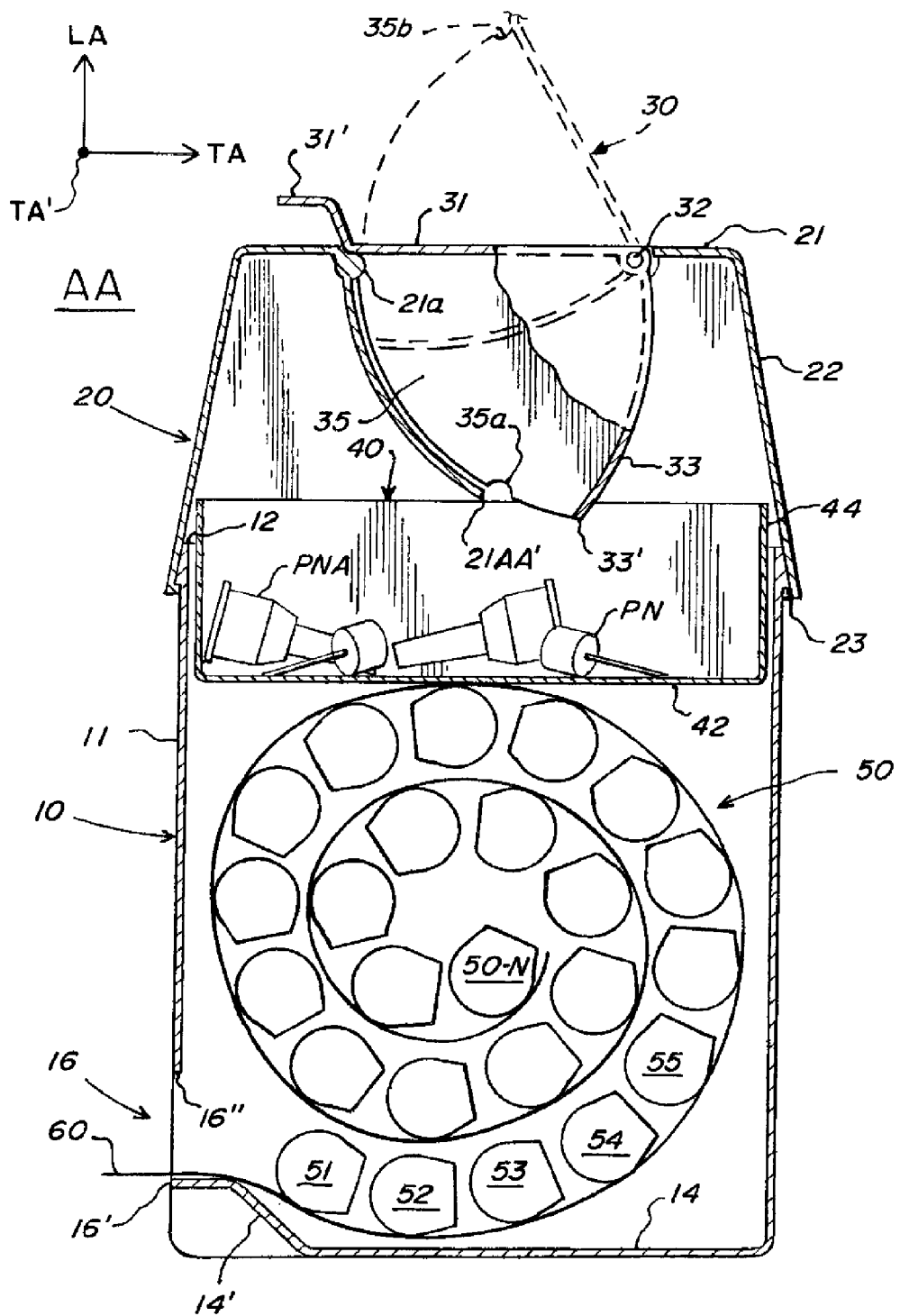
FIG. 1 is a side, cross-sectional view of a first embodiment of a sharps container provided by the invention.

The sharps container AA shown in FIG. 1 is depicted with a longitudinal axis LA and first and second transverse axes TA and TA', the three axes being mutually perpendicular. The container AA includes a receptacle 10, cover means 20, a dividing tray means 40 within the receptacle, and a manually operable means 30 in the cover means 20 for facilitating the sequential longitudinal disposal of individual used pen needle assemblies into the tray means 40. The receptacle 10 has a cup-like shape (with a pre-selected round or polygonal cross-section) with a side 11, an open top 12 and a bottom surface 14. An exit opening 16 is provided in side 11 near the bottom surface 14 and is sized by edges 16' and 16" to facilitate sequential transverse withdrawal therethrough of unused pen needle assemblies 50 stored beneath the bottom 42 of dividing tray means 40 in the bottom portion of the receptacle 10. Edge 16' is at the end of an upturned portion 14' of the bottom surface 14. The plurality of PNAs 50 are shown in FIG. 1 oriented on the cylindrical side of the outer shield, spaced-apart a preselected amount, and attached to a flexible tape means 60 (see also FIG. 1B) by suitable means such as an adhesive. The plurality of PNAs 50 are configured into a coil as is clearly shown in FIG. 1. The PNA closest to the exit opening 16 is identified by reference 51; the next four, in spaced-apart sequence, by references 52, 53, 54, and 55. The last PNA 50-N is at the end of the tape means 60 at the center of the coiled assembly of PNAs. The depicted attachment of the individual PNAs to the flexible tape 60 is space efficient and facilitates the storage of a large number of PNAs in a given space.

The manually operable means 30 in the cover means 20 is similar to a cover means 30 of the Applicant's copending U.S. patent application, Ser. No. 10/862,544; filed Jun. 7, 2004 and the same is incorporated herein for reference. Briefly, the cover means 30 is a cup-like device rotatably mounted on cover means 20 for rotation about a transverse axis between a closed position (solid in FIG. 1) and an open position (dashed lines in FIG. 1). When the cup is in the open position, then used PNAs and pen needles PNs may be sequentially placed within the cup. The cup is then rotated to its closed position which then opens up a pre-determined space or open gap between the bottom edge 33' of the bottom 33 of the cup and the bottom edge 21AA' of a baffle means 21AA; the aforesaid used PNAs and PNs pass through said space or gap to be collected by the dividing tray means 40.

Figure 1A:
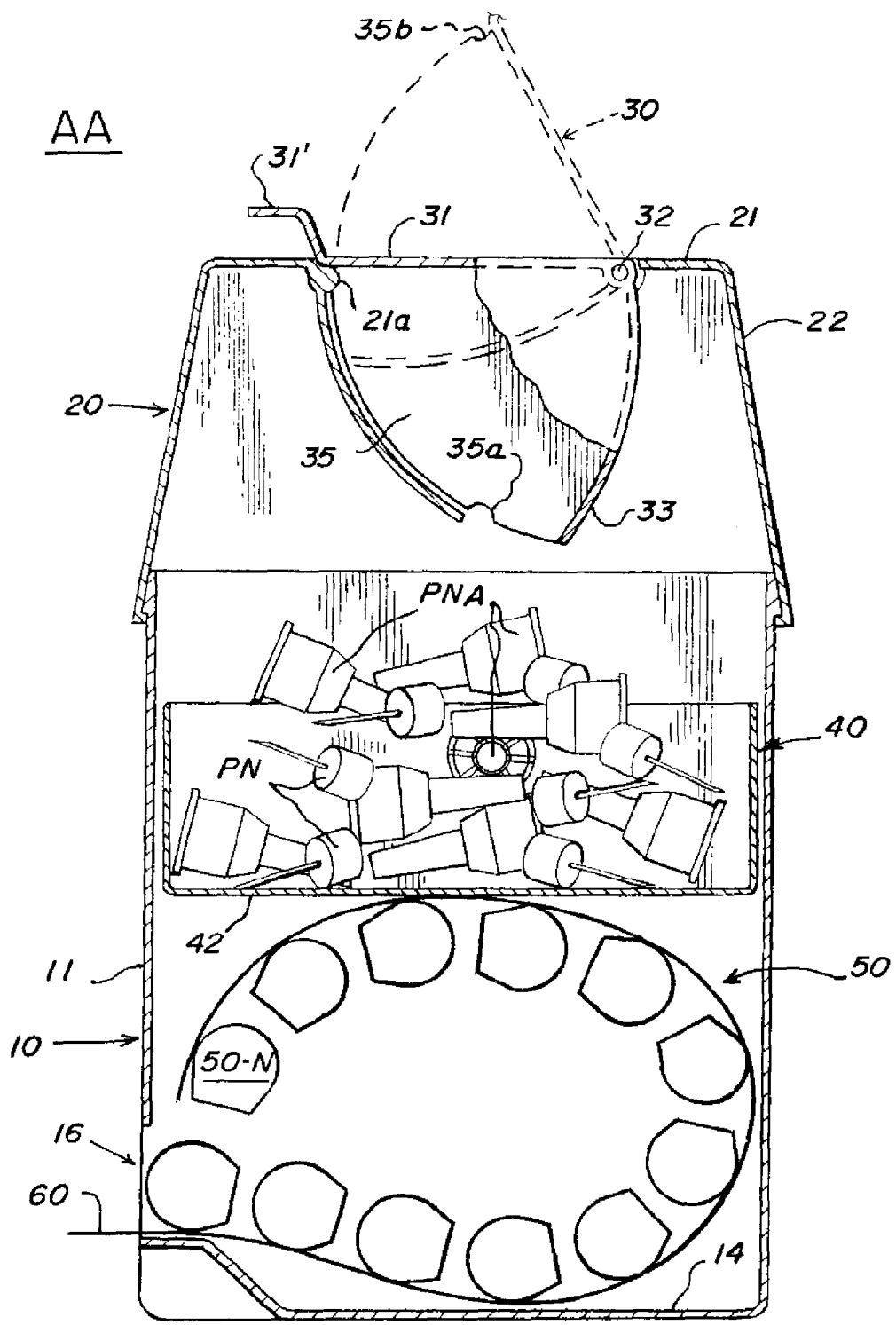
FIG. 1A is a side, cross-sectional view of the container of FIG. 1 with a substantial number of unused pen needle assemblies having been removed from the receptacle accompanied by the dividing tray means having moved longitudinally down toward the bottom of the receptacle.

FIG. 1A shows the same sharps container AA as FIG. 1 but with many of the unused PNAs already dispensed by being pulled out of exit opening 16 on the flexible tape 60. As the unused PNAs are removed from the receptacle 10, the dividing tray means 40 descends longitudinally as space becomes available.

Figures 1B, 2:
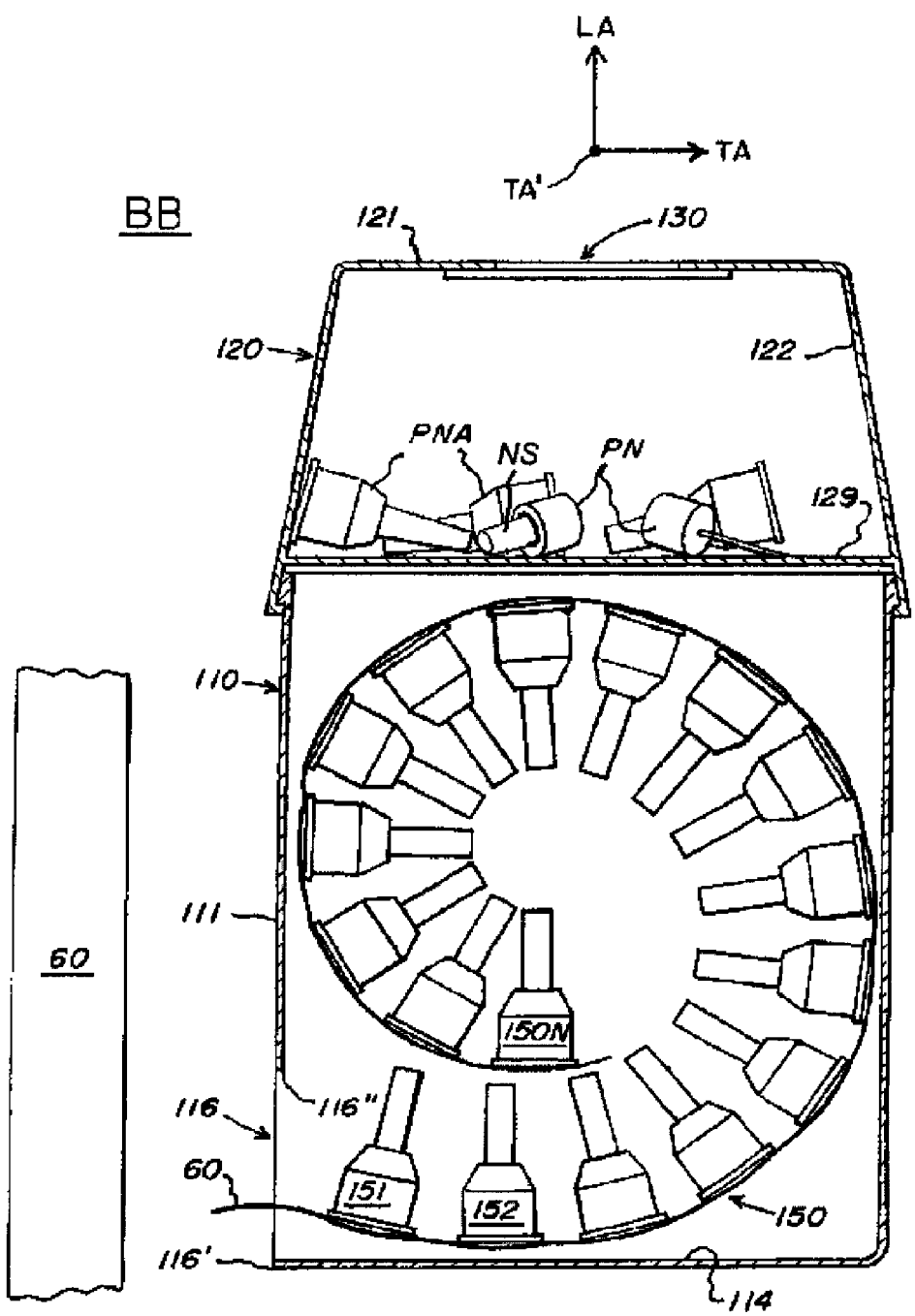
FIG. 1B is a plan view of a section of a flexible tape 60 used in the unused pen needle assembly dispensing means shown in FIGS. 1 and 2.
FIG. 2 is a side, cross-sectional view of another embodiment of the invention.

FIG. 2 shows an alternate sharps container BB comprising a receptacle 10, a cover means 120, an used PNA and/or PN disposal means 130, a partition 129 integral with cover means 120 to define a used PNA and/or PN and/or PN outer cylindrical shield storage space, and a coiled plurality 150 of unused PNAs: 151, 152 . . . 150N attached at the proximal ends thereof to a flexible tape means 60 within the receptacle 110. An exit opening 116 in side 111 of the receptacle facilitates the sequential series removal of the PNAs attached to the tape. The disposal means 130 is the same as the disposal means 130 of the sharps container DD shown in FIG. 5 comprising a plurality of flexible tabs 131 arranged in a generally circular configuration, being attached at the outer or radial extent to the cover and being longitudinally displaceable at their tips so as to facilitate the longitudinal passage therethrough of used PNAs and/or PNs and/or PN outer cylindrical shields.

Figure 3:
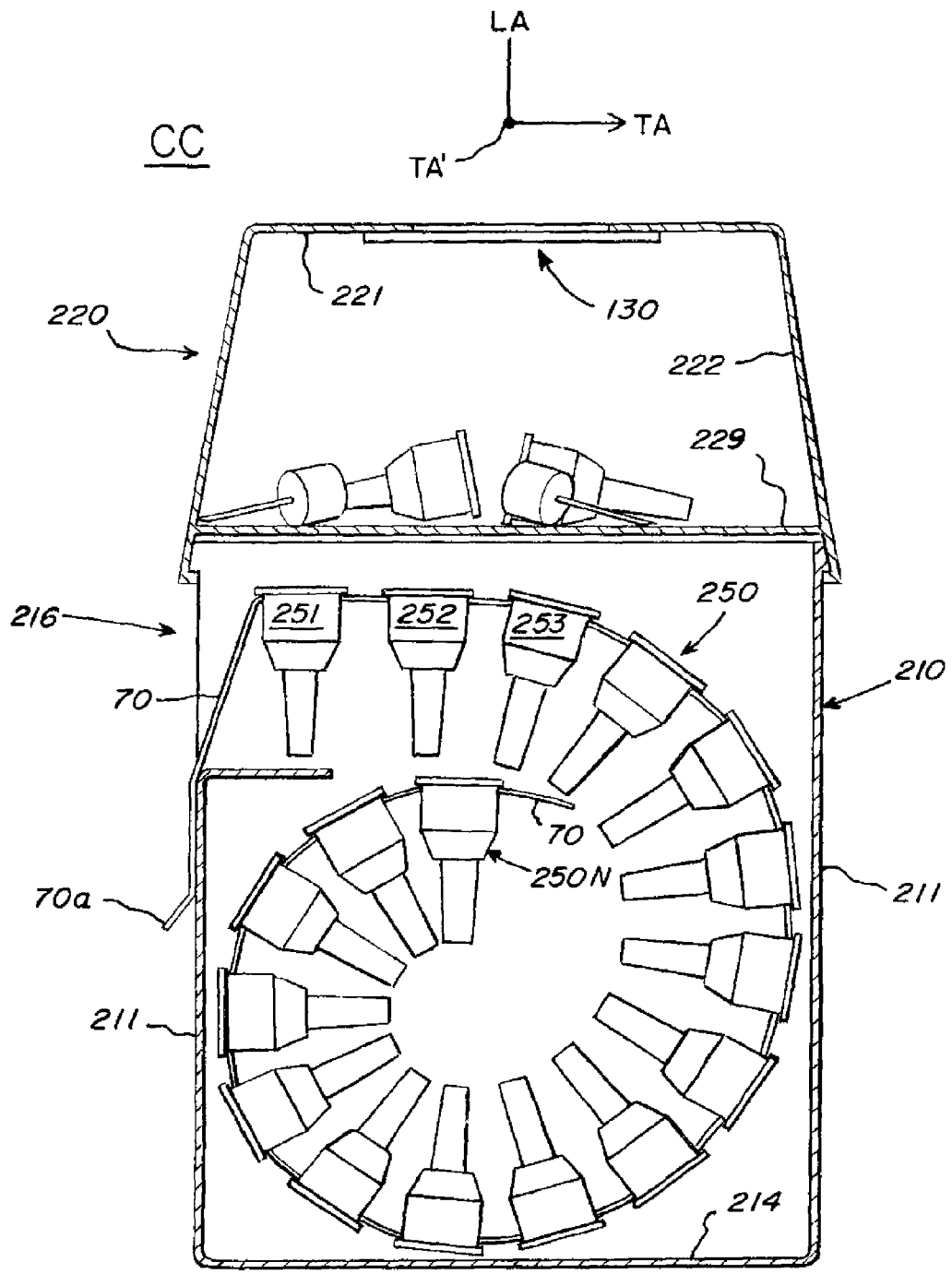
FIG. 3 is a side, cross-sectional view of another embodiment of the invention.
Figures 4, 5:
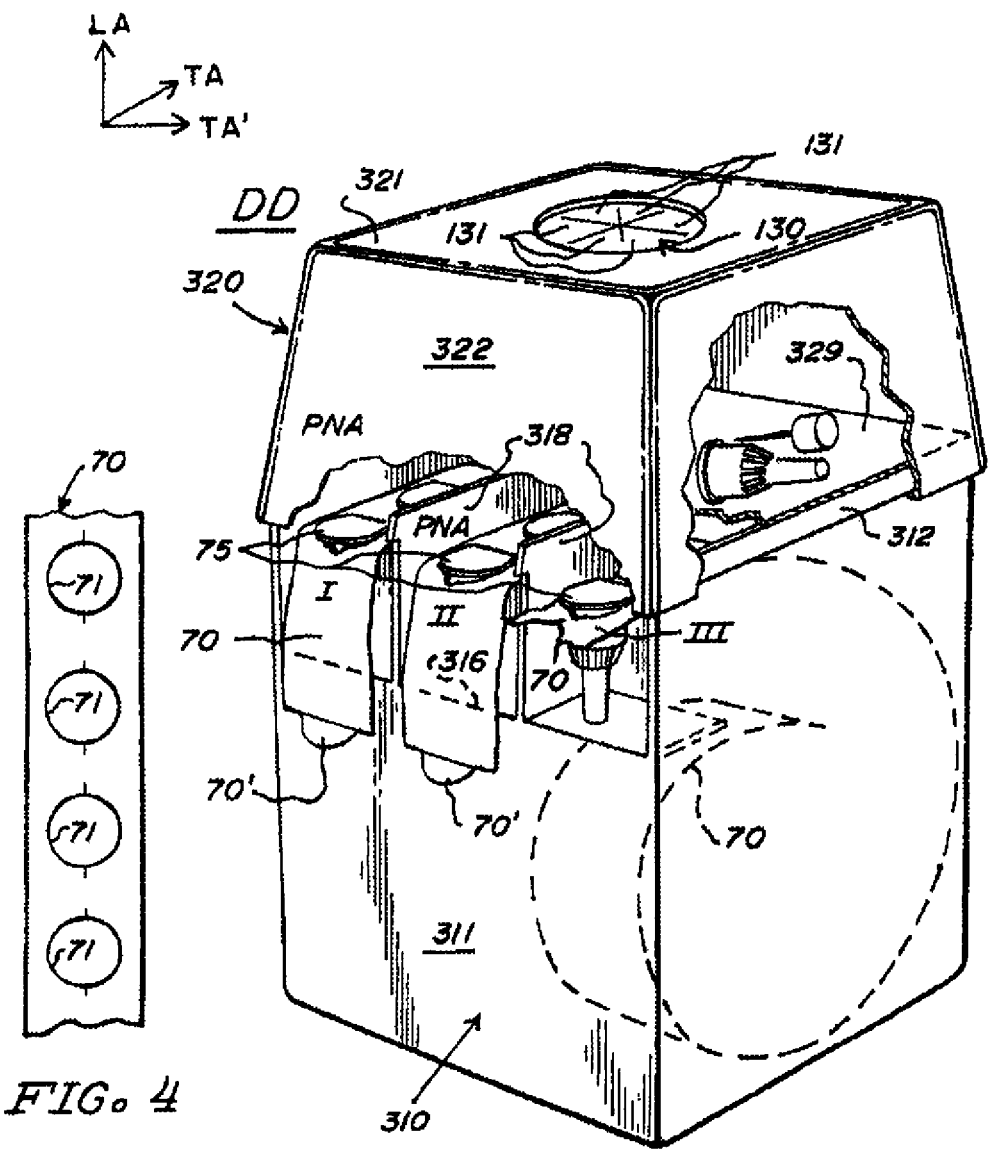
FIG. 4 is a plan view of a section of flexible tape means 70 used to hold a plurality of pen needle assemblies as shown in the containers depicted in FIGS. 3 and 5.
FIG. 5 is an isometric view (partly in section) of another embodiment of a sharps container provided by the invention.

FIG. 3 shows another alternate sharps container CC comprising a receptacle 210, a cover means 220 including a bottom positioned partition 229 (to define a used PNA and/or PN and/or PN outer cylindrical shield storage space), an used PNA and/or PN and/or PN outer cylindrical shield disposal means 130 (above described), and a coiled plurality 250 of unused PNAs 251, 252, 253 . . . 250N attached to a flexible tape means 70 by being inserted in spaced-apart apertures or openings 71 in the tape means 70 as is shown in FIG. 4. Thus the openings 71 are sized to snuggly receive the outer diameter of the safety shield of a PNA. The receptacle 210 has sides 211, a bottom 214, and an exit opening 216 near the top of the receptacle. The coil of PNAs are shown oriented so that the first PNA 251 is adjacent the exit opening 216 and is held in "ready" position by the end 70a of the flexible tape means 70 being detachably connected to the side 211 of the receptacle. Thus this embodiment of the invention also provides a sharps container (i) for the safe transportation and safe sequential dispensing of a large number of unused pen needle assemblies, and (ii) the safe sequential feeding of used PNAs and/or PNs into the above described used PNA and/or PN storage space.

The sharps container DD shown in FIG. 5 is a modification of the apparatus shown in FIG. 3 comprising a receptacle 310, a cover means 320 including a side 322 and a bottom-positioned partition 329 (to define a used PNA and/or PN storage space), the above described used PNA and/or PN disposal means 130, and three transversely spaced-apart coils of PNAs I, II and III, each having unused PNAs connected to flexible tapes 70 similar to the arrangement shown in FIG. 3. Tape ends 70' are shown for coils I and II and are detachably connected to the side 311 of the receptacle by releasable adhesive 316. The coils are separated by panels 318. The sides 322 of the cover 320 lock onto the top 312 of the receptacle. In some embodiments, each unused PNA outer shield 28 may include a removable thin sterile seal 75 covering the proximal (large diameter) end of the said outer shield.

When the user of the disclosed embodiments of sharps containers wants to safely and hygienically dispose of used PNAs and/or PNs, the preferred procedure is to transfer the entire container to an approved disposal means or site without attempting to remove the cover from the receptacle. As described, the covers have locking means which are intended to prevent or at least impede access to the used sharps or containers therefore.

While the preferred embodiment of the invention has been shown, it will be understood that variations may be made without departing from the inventive concept. It should, as an example, be understood that the term "pen needle assembly" (PNA) be interpreted to cover (i) a complete assembly including the above described cylindrical housing and axially extending needle with associated needle shield and outer shield, as well as (ii) the aforesaid assembly sans one or both shields and/or the shields. Accordingly, the invention is to be limited only by the scope of the following claims.

What is claimed:

1. A dispensing strip for needle assemblies, comprising:
   a thin flexible strip having a width and a length;
   a plurality of needle assemblies each having a longitudinal axis and comprising a needle and a shield for the needle; and
   a plurality of cavities associated with the thin flexible strip, said cavities being distributed along the length of the strip, extending from a single face of the strip, and sized to substantially contain a single needle assembly,
   wherein each cavity substantially contains a single needle assembly.

2. The dispensing strip of claim 1, wherein the axes of the plurality of needle assemblies and the cavities containing the needle assemblies are oriented substantially normal to both the width and length of the strip.

3. The dispensing strip of claim 2, wherein the width of the thin flexible strip is greater than the width of the cavities.

4. The dispensing strip of claim 1, wherein the axes of the plurality of needle assemblies and the cavities containing the needle assemblies are oriented substantially transverse to length of the strip.

5. The dispensing strip of claim 4, wherein the width of the strip is greater than the width of the cavities.

6. The dispensing strip of claim 1, further comprising a region of reduced tear resistance disposed between adjacent cavities along the thin flexible strip.

7. The dispensing strip of claim 1, wherein each cavity is sealed with a removable cover.

8. The dispensing strip of claim 1, wherein the strip has a configuration in which all dimensions of the configuration are less that the length of the strip.

9. The dispensing strip of claim 1, wherein the needle assemblies are pen needle assemblies.

10. The pen needle assemblies of claim 9 wherein each shield is sealed with a removable cover.

11. The dispensing strip of claim 1, wherein one end of the strip further comprises a releasable adhesive portion.

\* \* \* \* \*